United States Patent
Cousin et al.

(10) Patent No.: US 10,433,564 B2
(45) Date of Patent: Oct. 8, 2019

(54) METHODS FOR ANIMAL ANESTHESIA EMPLOYING RECYCLING OF THE GASES

(71) Applicant: L'Air Liquide, Societe Anonyme pour l'Etude et l'Exploitation des Procedes Georges Claude, Paris (FR)

(72) Inventors: Franck Cousin, Saint Brevin les Pins (FR); Robert Ian Taylor, Wavre (BE); Etienne Charve, Vanves (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 16/155,005

(22) Filed: Oct. 9, 2018

(65) Prior Publication Data
US 2019/0110486 A1    Apr. 18, 2019

(30) Foreign Application Priority Data
Oct. 17, 2017  (FR) .................................... 17 59716

(51) Int. Cl.
*A22B 3/00*    (2006.01)
*A61M 16/18*    (2006.01)
(Continued)

(52) U.S. Cl.
CPC ............... *A22B 3/005* (2013.01); *A22B 3/00* (2013.01); *A61D 7/04* (2013.01); *A61M 16/01* (2013.01); *A61M 16/0891* (2014.02); *A61M 16/186* (2013.01); *A61M 16/0045* (2013.01); *A61M 16/0075* (2013.01); *A61M 16/0081* (2014.02); *A61M 16/12* (2013.01);
(Continued)

(58) Field of Classification Search
CPC .................................. A22B 3/005; A22B 3/00
USPC ....................................................... 452/52, 66
See application file for complete search history.

(56) References Cited

U.S. PATENT DOCUMENTS 5,112,270 A * 5/1992 Howard .................... A22B 3/02
                                                          452/57
6,126,534 A * 10/2000 Jacobs ...................... A22B 3/00
                                                          452/66
(Continued)

FOREIGN PATENT DOCUMENTS

FR         2 914 864        10/2008
WO     WO 2004/098297       11/2004
(Continued)

OTHER PUBLICATIONS

French Search Report and Written Opinion for FR 1 759 716, dated Jun. 12, 2018.

*Primary Examiner* — Richard T Price, Jr.
(74) *Attorney, Agent, or Firm* — Christopher J. Cronin

(57) ABSTRACT

The invention relates to a method for anaesthetizing animals before slaughter, by the anesthetic action of gases or gas mixtures, operated in "batch" mode, in which the live animals, preferably put together in one or more cages, are placed in a lock chamber for treatment where the animals are brought into contact with anesthetic gas, following a cycle comprising several steps characterized by different contents of anesthetic gas, characterized in that at least one of the steps is carried out using gas recovered from the lock chamber and stored in at least one capacity (2, No. 1, No. 2 etc.) for temporary storage having a variable volume.

6 Claims, 1 Drawing Sheet

(51) Int. Cl.
*A61D 7/04* (2006.01)
*A61M 16/01* (2006.01)
*A61M 16/08* (2006.01)
 A61M 16/12 (2006.01)
 A61M 16/00 (2006.01)
(52) U.S. Cl.
 CPC .............. *A61M 2202/0208* (2013.01); *A61M 2202/0225* (2013.01); *A61M 2202/0283* (2013.01); *A61M 2250/00* (2013.01)

(56) References Cited

U.S. PATENT DOCUMENTS 7,448,943 B1\* 11/2008 Woodford .............. A22B 3/005
 452/66
8,323,080 B2\* 12/2012 Lang ...................... A22B 3/086
 452/57

FOREIGN PATENT DOCUMENTS

| WO | WO 2005/058049 | 6/2005 |
| WO | WO 2008/128027 | 10/2008 |
| WO | WO 2016/193368 | 12/2016 |

\* cited by examiner

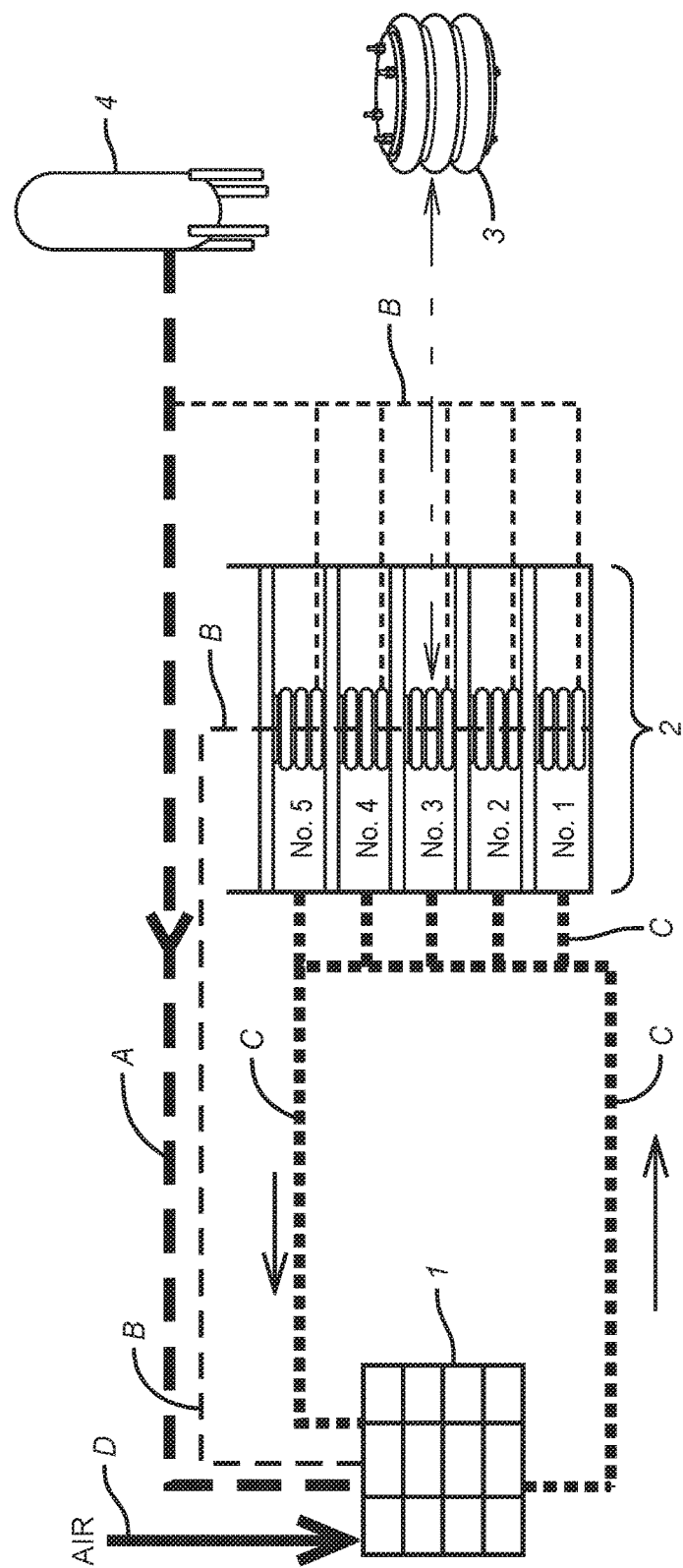

METHODS FOR ANIMAL ANESTHESIA EMPLOYING RECYCLING OF THE GASES

CROSS-REFERENCE TO RELATED APPLICATIONS

This application claims the benefit of priority under 35 U.S.C. § 119 (a) and (b) to French patent application No. FR 1 759 716, filed Oct. 17, 2017, the entire contents of which are incorporated herein by reference.

BACKGROUND

Field of the Invention

The present invention relates to the field of animal anesthesia, and notably anesthesia of mammals or gallinaceae before slaughter. Anesthesia ensures that the animal is unconscious at the time of slaughter.

The question of animal welfare and the well-being of personnel is at the heart of the concerns of the test institutes, as is the cost of the method of anesthesia for the abattoir.

Related Art

It is known that in this industry there are essentially 3 methods of anesthesia: electrical anesthesia, stunning by mechanical shock and anesthesia by supply of a gas, most often $CO_2$ in gaseous form.

Anesthesia by supply of $CO_2$ is commonly applied in the following conditions:
treatment of species, in particular of gallinaceae, is carried out in batch mode;
the cages of live animals arrive at the place of slaughter in boxes;
each box (therefore containing an arrangement of cages) is taken out of the lorry, carried into the place of slaughter, introduced into a lock chamber (or cell) for treatment using the anaesthetic gas, brought out of the lock chamber once the treatment has been carried out, sent to the line for slaughter of the animals (the animals are positioned upside down on moving hooks etc.)—all by means for automatic handling.

The main advantages of $CO_2$ may be summarized as follows:
group anesthesia reduces animal stress;
decrease in petechiae;
absence of physical intervention of the personnel on the animal to render it unconscious;
handling of the animals in a state in which they are unconscious.

The main drawbacks of $CO_2$ may be summarized as follows:
loss of $CO_2$ on opening the doors of the lock chambers;
constant demands for optimization of the time of discomfort of the animal;
throughput rates lower than with the other known methods of anesthesia;
solutions are available for recycling of $CO_2$ by filtration and concentration, but they involve high capital costs and high costs of electric power.

SUMMARY OF THE INVENTION

Thus, in the context of the present invention, a method of anesthesia is proposed using a gas or gas mixture, which will be recycled, allowing consumption of the gas to be optimized, while reducing animal stress. For this, it is proposed to recycle the gas using temporary storage means (which may be called capacities), these storage means being, as will be seen, of variable volume.

In fact, for animal welfare and the final quality of the products, the anesthesia cycle generally comprises several steps: for example loading the animals, then gradual increase in content for stunning, followed by a higher content to reach lethal thresholds, and finally stabilization at these thresholds for a predetermined time (notably depending on the species treated), before unloading to go to slaughter.

As each of these steps employs different levels of gas, and for example different levels of $CO_2$, it is advantageous to store the recycled gas in specific reserves.

To illustrate this, for example the following stocks may be held:
a reserve of gas that consists of ambient air or else is similar in composition to ambient air;
a reserve of gas comprising about 20% of $CO_2$;
a reserve of gas comprising about 40% of $CO_2$;
a reserve of gas comprising about 60% of $CO_2$;
the rest of the composition being air, for example.

BRIEF DESCRIPTION OF THE FIGURES

FIGURE is a schematic of an embodiment of the invention.

DETAILED DESCRIPTION OF THE INVENTION

The accompanying FIG. 1 illustrates one of the preferred embodiments of the invention, showing the following elements:
reference 1 denotes a lock chamber or cell in which the cages containing the animals to be anaesthetized are placed;
reference 2 denotes a set consisting here (but this is only one example) of 5 compartments (or "capacities") for gas storage, of variable capacity (these capacities may also be called "accordions" or "bellows");
the detail view 3 on the right-hand side of the FIGURE shows details of the system that allows the volume of a capacity to be changed (in the case illustrated here: a pneumatic bulb (jack));
reference 4 denotes gas storage, for example liquid $CO_2$;
and the following symbols have been used for better visualization of the various movements of gas occurring in this embodiment of the invention:
at the extreme left of the FIGURE, a large black arrow denotes arrival of air "only" or "pure" in the lock chamber 1 (circuit D);
letter A (thick dashes) denotes arrival (or supplement) of pure $CO_2$ in the lock chamber 1;
letter B (thin dashes) denotes pressurization of the bulbs with pure $CO_2$, and depressurization of the bulbs towards the lock chamber;
letter C (dotted line) denotes the circuit for recycling the $CO_2$ between the lock chamber and the assembly 2 of capacities.

An embodiment example of the installation in FIG. 1 will now be described, for better understanding of what the invention provides, while bearing in mind of course that the times and the levels of exposure to the gases will have to be adapted according to the animal species treated, or their weight, their age etc. An example using $CO_2$ is illustrated below.

During commissioning, i.e. on first use, $CO_2$ is injected gradually into the lock chamber 1 (circuit A).

During this first use, anesthesia is carried out with non-recycled ("pure") gas, therefore not with gas that has been stored in the assembly 2, but of course this gas injected for the first use will not be lost, it will, as will be seen, be stored in the capacities 2 in order to be used in the next cycle, and so on.

At this stage, the lock chamber therefore comprises a high $CO_2$ content, and the aim is to aspirate this high concentration as well as possible. To segment the different gas contents desired, several gas storage compartments are used (in the example given here, from No. 1 to No. 5).

For example, compartment No. 1 first aspirates (for aspiration, $CO_2$ is injected into the corresponding bulb 3 (circuit B)), the accordion rises and generates a negative pressure, which aspirates gas contained in the lock chamber (circuit C).

This will give a better understanding of the extremely advantageous nature of the technical proposition of the invention, of a capacity with variable volume, thus making it possible to create the negative pressure and aspiration of the gas contained in the lock chamber.

The aspiration may advantageously be qualified using a gas analyser. As an illustration, at 50% of $CO_2$ in compartment. No. 1 we switch to compartment. No. 2 according to the approach described above.

A compartment is overdimensioned in volume so as not to disturb the procedure and with filling of the compartments by switching to the next compartment without having reached the target value.

A compartment that is sufficiently filled is sealed with a leak-proof valve.

When we switch to compartment. No. 2, we wish for example to fill the latter with a gas with lower content than. No. 1. For this, ambient air is injected into the lock chamber, or else a valve is opened which will allow fresh air to be aspirated.

To raise bulb. No. 2 again, $CO_2$ is injected into this bulb.

Preferably, injection of air will be carried out opposite the point of aspiration. In the case of a gas with a high density such as $CO_2$, aspiration in the bottom of the lock chamber is preferred, and injection of air at the top of the lock chamber.

With compartment 2 filled, we move on to 3 and then 4 and finally 5.

Once the treatment has been carried out, and therefore following opening of the lock chamber to remove the animals and introduce a new batch, the lock chamber 1 therefore has a low content of anaesthetic gas (in fact close to ambient air). It is then preferred to inject gas into the lock chamber gradually.

It is then preferable to begin with the compartment with the lowest concentration of anaesthetic gas (here, in the example described above. No. 5).

As the process of anesthesia is based on a time/gas content pair, an analyser coupled to time regulation will advantageously be able to control the opening of the various compartments to achieve the necessary gas values (opening of bulbs. No. 5 to. No. 1).

To release the gas from a compartment, it is necessary to open the corresponding valve but also purge the bulb, and since the gas used for actuating the jack is precisely the anaesthetic gas it will advantageously be released into the lock chamber to be reused.

This ploy makes it possible to take advantage of the pressure that is said to be "free" (the pressure available typically being between 11 and 20 bar) to actuate the jacks without using additional energy (which would be electrical or from compressed air).

To replace the air present in the lock chamber for treatment with the anaesthetic gas it is necessary to open a purge valve (circuit D).

For safety reasons, it is preferable to set up an arrangement in which injection of gas is only possible if the lock chamber is filled with the boxes making up the batch; in that way no person can be present in the lock chamber during injection.

The following is an example of the case of poultry for meat:

removal of the preceding cages and introduction of a batch (2 min without injection);
then 1 min to increase to 20%;
then 2 min to reach 35%;
then 2 min to reach approximately 75%;
1 min 30 s of stabilization at this content close to 75%;
one minute for returning to 0% of $CO_2$.

The present invention thus relates to a method for anaesthetizing animals before slaughter, by the anaesthetic action of gases or gas mixtures, said method operating in "batch" mode in which the live animals, preferably put together in one or more cages, are placed in a lock chamber for treatment where the animals are brought into contact with the anaesthetic gas or gas mixture, following a cycle comprising several steps characterized by different contents of anaesthetic gas, characterized in that at least one of the steps is carried out using gas recovered from the lock chamber and stored in at least one variable-volume temporary storage capacity.

According to one of the embodiments of the invention, recovery of the gas contained in the lock chamber is carried out by an aspiration system of the bellows (or accordion) type, said bellows system providing the variable character of the volume of the capacity, where anaesthetic gas is injected into a bulb (jack) associated with the capacity in question, causing the bellows to rise, thus generating a negative pressure that will allow aspiration of the gas present in the lock chamber, the gas used for actuating the bulb preferably being released subsequently in the lock chamber to be reused (not lost).

According to one of the embodiments of the invention, there are several storage capacities, for storing different contents of anaesthetic gas in a carrier gas, for example air, ranging from a lowest content to a highest content.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising."

"Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A method for anaesthetizing animals before slaughter using an anaesthetic gas or gas mixture, said method operating in "batch" mode in which the live animals, put together in one or more cages, are placed in a lock chamber for treatment where the animals are brought into contact with the anaesthetic gas or gas mixture, following a cycle comprising several steps using different contents of anaesthetic gas, wherein at least one of the steps is carried out using gas recovered from the lock chamber and stored in at least one variable volume temporary storage compartment.

2. The method of claim 1, wherein:
   the at least one variable volume temporary storage compartment intended to receive the recovered gas is provided with a bellows system; and
   recovery of gas contained in the lock chamber is carried out by the bellows system by injecting anaesthetic gas into a bulb operatively associated with the at least one variable volume temporary storage compartment, causing the bellows to rise, thus generating a negative pressure that will allow aspiration of the gas present in the lock chamber, the gas used for actuating the bulb being released subsequently in the lock chamber in order to be reused.

3. The method of claim 1, wherein there are several compartments for temporary storage having a variable volume, thereby allowing separate storage of different contents of anaesthetic gas in a carrier gas.

4. An installation for anaesthetizing animals before slaughter, by the anaesthetic action of gases or gas mixtures, operating in "batch" mode, comprising a lock chamber for treatment where the animals are brought into contact with the anaesthetic gas or gas mixture and at least one variable volume temporary storage compartment being able to recover gas in the lock chamber and store such recovered gas for later use for anesthesia.

5. The installation of claim 4, wherein:
   said compartment intended to receive the recovered gas from the lock chamber is provided with a bellows system,
   a bulb or jack is associated with said compartment, recovery of the gas contained in the lock chamber being carried out by injecting anaesthetic gas into the bulb associated with the capacity in question, causing the bellows to rise, thus generating a negative pressure that will allow aspiration of the gas present in the lock chamber, the gas used for actuating the bulb preferably being released subsequently in the lock chamber in order to be reused.

6. The installation of claim 4, wherein said one or more variable volume temporary storage compartment comprises several variable volume temporary storate compartments, thereby allowing separate storage of different contents of anaesthetic gas in a carrier gas.

\* \* \* \* \*